US006214613B1

(12) United States Patent
Higuchi et al.

(10) Patent No.: US 6,214,613 B1
(45) Date of Patent: Apr. 10, 2001

(54) EXPRESSION SCREENING VECTOR

(75) Inventors: Kazuo Higuchi; Kimiyoshi Kanno, both of Fuji (JP)

(73) Assignee: Ashai Kasei Kogyo Kabushiki Kaisha, Osaka (JP)

(*) Notice: Subject to any disclaimer, the term of this patent is extended or adjusted under 35 U.S.C. 154(b) by 0 days.

(21) Appl. No.: 08/647,924

(22) PCT Filed: Dec. 2, 1994

(86) PCT No.: PCT/JP94/02033

§ 371 Date: Jul. 12, 1996

§ 102(e) Date: Jul. 12, 1996

(87) PCT Pub. No.: WO95/15393

PCT Pub. Date: Jun. 8, 1995

(30) Foreign Application Priority Data

Dec. 3, 1993 (JP) .................................................... 5-303620

(51) Int. Cl.[7] .............................. C12N 15/00; C12Q 1/70; G01N 33/53; C12P 21/08
(52) U.S. Cl. ............................ 435/320.1; 435/5; 435/7.1; 435/6; 435/252.3; 530/387.1; 530/387.3; 536/23.1; 536/23.4; 536/23.5; 536/23.53; 935/22; 935/23; 935/26; 935/31
(58) Field of Search ............................... 530/387.1, 387.3; 536/23.1, 23.4, 23.5, 23.53; 435/320.1, 252.3, 240.2, 6, 7, 7.1, DIG. 1, DIG. 3, DIG. 4, DIG. 15, DIG. 46, DIG. 47; 935/22, 23, 26, 31, 52, 66, 72, 79

(56) References Cited

U.S. PATENT DOCUMENTS 5,079,173 * 1/1992 Noto et al. .
5,270,458 * 12/1993 Leminska .
5,395,750 * 3/1995 Dillon et al. .

FOREIGN PATENT DOCUMENTS

WO 88/06630 9/1988 (WO) .
WO 91/13160 9/1991 (WO) .
WO 92/18619 10/1992 (WO) .
WO 93/01287 1/1993 (WO) .
WO 93/10214 5/1993 (WO) .

OTHER PUBLICATIONS

Parkinson et al, "Stable Expression of a secretable deletion mutant of recombinant human thrombomodulin in mammalian cells" J Biol Chem 265(21) pp. 12602–10 (Abstract), Jul. 25, 1997.*

Suzuki et al "Structure and Expression of human thrombomodulin, a thrombin receptor on endothelium acting as a cofactor for protein kinase c activation" Embo J 6(7) pp. 1891–7 (Abstract), Jul. 1987.*

J. S. Andris et al., "Probing the human antibody repertoire to exogenous antigens", pp. 4053–4059, Journal of Immunology, vol. 149, No. 12, Dec. 15, 1992.

K. Higuchi et al., "Cell display library for gene cloning of variable regions of human antiobodies to hepatitis B surface antigen", pp. 193–204, Journal of Immunological Methods, vol. 202, No. 2, Mar. 28, 1997.

K. Suzuki et al., "Structure and expression of human thrombomodulin, a thrombin receptor on endothelium acting as a cofactor for protein C activation", pp. 1891–1897, The Embo Journal, vol. 6, No. 7, Jul. 7, 1987.

S. L. Zebedee et al., "Human combinatorial antibody libraries to hepatitis B surface antigen", pp. 3175–3179, Proc. National Acad Science USA, vol. 89, Biochemistry, Apr. 1992.

Sambrook et al "Molecule Cloning, A Laboratory Manual, Second edition" Cold Spring Harbor Laboratory Press, USA pp. 5.28–5.29, 16.3–16.7, 1989.*

Xiang et al., "Production of Murine V–Human Crl Chimeric Anti–Tag72 Antibody Using V Region cDNA Amplified by PCR", *Molecular Immunology*, vol. 72, No. 8, 1990, pp. 809–817.

Bebbington et al., "High–Level Expression of a Recombinant Antibody from Myeloma Cella Using a Glutamine Synthetase Gene as an Amplifiable Selectable Marker", *Biotechnology*, vol. 10, Feb. 1992, pp. 169–175.

(List continued on next page.)

Primary Examiner—J. Venkat
Assistant Examiner—P. Ponnaluri
(74) Attorney, Agent, or Firm—Young & Thompson

(57) ABSTRACT

An expression vector for preparing a library of an antibody variable region, which can express comprising polypeptides containing the H-chain and/or L-chain variable regions of antibodies in the membrane-bound form on the surfaces of eukaryotic cells, which is containing the nucleotide sequence of AKL (formula 1) and/or the nucleotide sequence AKH (formula 2), and which is replicable in the cells:

$$5'\text{-}P_L\text{-}S_L\text{-}C_L\text{-}M_L\text{-}A_L\text{-}3' \quad \text{(formula 1)(AKL)}$$

$$5'\text{-}P_H\text{-}S_H\text{-}C_H\text{-}M_H\text{-}A_H\text{-}3' \quad \text{(formula 2)(AKH)}$$

wherein $P_L$ and $P_H$ represent a promoter, respectively; $S_L$ and $S_H$ represent a nucleotide sequence coding for a signal peptide respectively; $C_L$ represents a nucleotide sequence coding for the L-chain constant region of an antibody; $C_H$ represents a nucleotide sequence coding for the H-chain constant region of an antibody or a nucleotide sequence coding for a polypeptide containing at least CH1 of the H-chain constant region of an antibody; $A_L$ and $A_H$ represent a polyadenylation signal, respectively; "5'-" and "-3'" refer to the 5' side and the 3' side, respectively, of the nucleotide sequence; and $M_L$ and $M_H$ represent a nucleotide sequence coding for the transmembrane domain, respectively, while either $M_L$ or $M_H$ may be a mere chemical bond when the expression vector contains the nucleotide sequence of AKL and AKH. Cloning site of $R1_L$, $R2_L$, $R1_H$ and $R2_H$ is present within or in the vicinity of $S_L$, $C_L$, $S_H$ and $C_H$ respectively, in order for the nucleotide sequences coding for the L-chain and H-chain variable regions to be readily inserted in between $S_L$ and $C_L$, and $S_H$ and $C_H$ respectively.

17 Claims, 7 Drawing Sheets

OTHER PUBLICATIONS

Huse et al., "Generation of a Large Combinatorial Library of the Immunoglobulin Repertoire in Phage Lambda", *Research Article*, Dec. 1989, pp. 1275–1281.

McCafferty et al., "Phage Antibodies: Filamentous Phage Displaying Antibody Variable Domains", *Nature*, vol. 348, Dec. 1990, pp. 552–554.

Kang et al., "Linkage of Recogination and Replication Functions by Assembling Combinatorial Antibody Fab Libraries Along Phage Surfaces", *Proc. Natl. Acad. Sci. USA*, vol. 88, May 1991, pp. 4363–4366.

Anand et al., "Bacterial Expression and Secretion of Various Single–Chain Fv Genes Encoding Proteins Specific for a Salmonella Serotype B O–Antigen", *The Journal of Biological Chemistry*, vol. 266, No. 32, Nov. 1991, pp. 21874–21879.

Huston et al., "[3] Protein Engineering of Single–Chain Fv Analogs and Fusion Proteins", *Methods in Enzymology*, vol. 203, 1991, pp. 46–87.

Bird et al., "Single–Chain Antibody Variable Regions", *Tibtech*, vol. 9, Apr. 1991, pp. 132–137.

Tsumoto et al., "Effect of the Order of Antibody Variable Regions on the Expression of the Single–Chain Hyhel10 Fv Fragment in *E. Coli* and the Thermodynamic Analysis of its Antigen–Binding Properties", *Biochemical and Biophysical Research Communications*, vol. 201, No. 2, 1994, pp. 546–551.

Skerra et al., "Secretion and in vivo Folding of the $F_{ab}$ Fragment of the Antibody McPC603 in *Escherichia coli*: Influence of Disulphides and Cis–Prolines", *Protein Engineering*, vol. 4, No. 8, 1991, pp. 971–979.

Wood et al., "High Level Synthesis of Immunoglobulins in Chinese Hamster Ovary Cells ", *The Journal of Immunology*, vol. 145, No. 9, Nov. 1990, pp. 3011–3016.

Venkitaraman et al., "The B–Cell Antigen Receptor of the Five Immunoglobulin Classes", *Nature*, vol. 352, Aug. 1991, pp. 777–781.

Schable et al., "The Variable Genes of the Human Immunoglobulin x Locus", *Biol. Chem. Hoppe–Seyler*, vol. 374, Nov. 1993, pp. 1001–1022.

Williams et al., "Cloning and Sequencing of Human Immunoglobulin $V^\lambda$ Gene Segments", *Eur. J. Immunol.*, vol. 23, 1993, pp. 1456–1461.

Matsuda et al., "Structure and Physical Map of 64 Variable Segments in the 3' 0.8–Megabase Region of the Human Immunoglobulin Heavy–Chain Locus", *Nature Genetics*, vol. 3, Jan. 1993, pp. 88–94.

Cook et al., "A Map of the Human Immunoglobulin $V_H$ Locus Completed by Analysis of the Telomeric Region of Chromosome 14q", *Nature Genetics*, vol. 7, Jun. 1994, pp. 162–168.

Orlandi et al., "Cloning Immunoglobulin Variable Domains for Expression by the Polymerase chain Reaction", *Proc. Natl. Acad. Sci. USA*, vol. 86, May 1989, pp. 3833–3837.

Igarashi et al. "Electroporation", *Series Bio. Exoeriments 1*, pp. 163–175, with English translation.

Harada, "Panning Method", *Biomanual Series 3, geneCloning*, pp. 106–117, with English translation.

Hoshino, "V. Cell Sorting", *Flow Cytometry–Technique and Practice*, pp. 131–139, with English translation.

Hirt, "Selective Extraction of Polyoma DNA from Infected Mouse Cell Cultures", *J. Mol. Biol.*, vol. 26, 1967, pp. 365–369.

Kabat et al., *Sequences of Proteins of Immunological Interest*, Fifth Edition, 1991.

"Isolation Method of Lymphocyte", *New Bio. Exoeriments Series 12*, pp. 3–23, with English translation.

* cited by examiner

STRUCTURE OF IgG1   STRUCTURE OF scFV

1) GOAT ANTI HUMAN IMMUNOGLOBULIN ANTIBODY STAINING

2) BIOTIN LABELLED GK1.5 (RAT IgG2b)

ORDINATE : NUMBER OF CELLS
ABSCISSA : RELATIVE FLUORESCENCE INTENSITY

ORDINATE : NUMBER OF CELLS
ABSCISSA : RELATIVE FLUORESCENCE INTENSITY

EXPRESSION SCREENING VECTOR

This application is a 317 of PCT/JP94/02033, filed on Dec. 2, 1994.

BACKGROUND OF THE INVENTION

1. Field of the Invention

This invention relates to a vector which directs expression of an antibody or a portion of antibody at least containing an antigen binding site (hereinafter designated as antibodies) on the surface of cell membrane, in order to select a nucleotide sequence coding for a variable region of the antibody for a specific antigen (hereinafter designated as nucleotide sequence of variable region), a library and a method for selecting a nucleotide sequence of antigen-specific antibody variable region using the said vector, and a kit containing the same.

2. Description of the Related Art

Development of antibody for application in pharmaceuticals has recently progressed. Antibody of those pharmaceutical applications is preferably a human type due to antigenicity to the humans. However, preparation of human antibody to the specific antigen has not been established unlike mouse monoclonal antibody with established hybridoma method. From these points of view, a development for a new process applicable to the preparation of human monoclonal antibody in place of hybridoma method, has been expected.

Preparation of specific antibody for specific antigen by means of genetic engineering process, requires a nucleotide sequence of variable regions of the H- and L-chains which determine the antigen specificity of the antibody. Genetically engineered preparation of antibody using the variable region of the H- and L-chains has been known [Xiang, J. et al. (1990), Mol. Immun., 27, 809; Bebbington, C. R. et al. (1992), Biotechnology, 10, 169].

A method for preparing the nucleotide sequence of variable region of antigen-specific H- and L-chains, using *E. coli* phage or phagemid has been known [Huse. W. D. et al. (1989). Science, 246, 1275; McCafferty, J. et al. (1990), Nature, 348, 552 and Kang, A. S. et al. (1991), Proc. Natl. Acad. Sci. USA 88, 44363].

In these methods, antibody library is prepared by producing Fab (refer to FIG. 1) per se, or antibody library (phage antibody library) is prepared by producing fused phage coat protein with Fab or a single chain Fv, which is prepared by linking the H-chain variable region to the L-chain variable region of antibody with suitable linker (refer to FIG. 1, hereinafter designates as scFv), thus antigen-specific antibody and gene thereof are selected by means of binding affinity with antigen.

As explained hereinabove, phage antibody library is prepared by producing Fab or scFv by *E. coli*. Fab or scFv produced by *E. coli* form an inclusion body (in case of intracellular production), or is accumulated in the periplasm to form insoluble protein (in case of secretion) [Anand, N. N. et al. (1991), J. Biol. Chem., 266, 21874; Huston, J. S. et al. (1991), Methods Enzymol., 203, 46]. Inclusion body and insoluble protein should be solubilized to construct higher-order structure (renature) for obtaining protein with antigen-binding activity.

Preparation of scFv by linking the H-chain variable region to L-chain variable region with suitable linker in various antibodies, for which properties thereof were well known, using expression system of *E. coli* has been tried [Bird, R. E. et al. (1991), TIBTEC, 9, 132; Anand, N. N. et al. (1991), J. Biol. Chem., 266, 21874]. Affinity of the scFv is generally decreased as compared with that of Fab obtained by papain hydrolysis. Further productivity of scFv varies greatly by an order of the H- and L-chain variable regions [Tsumoto, K. et al. (1994), Biochem. Biophys. Res. Comm., 201, 546]. Therefore production of scFv of some antibodies by *E. coli* may show disadvantages. In the phage antibody system hereinbefore explained, the scFv is prepared to form fused protein with minor coat protein g3p of fd phage. Fused protein of some kind of scFv loses antigen-binding activity [Furuta, S. et al., a presentation at Japan. Biochem. Soc. Meeting, 1994].

As explained hereinabove, the expression of scFv or phage antibody using scFv in *E. coli* has various disadvantages and the case with mere success in preparation of an antibody does not warrant the success in all other cases of the antibodies. There are possibilities to be prepared incomplete library having problems such that the expressed variable region has a bias in variety and that affinity of the expressed antibody differs from that of the original.

A problem in expression of scFv in *E. coli* seems to be caused by artificial structure linking the H-chain variable region to the L-chain variable region with linker and, in addition to that, is thought to be mainly caused by cellular structure of *E. coli* which has no organella for constructing higher-order structure of protein such as endoplasmic reticulum in animal cells. Originally, since the active antigen-binding site of antibody can be formed by establishing exact steric structure containing intramolecular disulfide bonds in H-chain and L-chain, respectively, and by forming the one to one corresponding dusulfide bond of the H- and L-chains, the higher-order structure of protein is extremely important for the expression of activity.

Expression system for Fab on the surface of phage in place of scFv has the same problem. Considering the large size of molecular weight of Fab of about 45,000 as compared with that of scFv of about 26,000, and necessity of exact association with two polypeptide chains, an expression of Fab having exact activity will be more difficult than that of scFv. Expression of active Fab in *E. coli* shows less productivity [Skerra, A. et al. (1991) Protein Eng. 4, 971].

As explained in the above, a screening system in use of *E. coli* is not preferable for expression of protein having complex higher-order structure such as antibody which is originally produced in animal cells. Accordingly, the expression screening system in use of eukaryotic cells, especially animal cells, is thought to be preferable. Expression system in use of animal host cells shows no problems as like in the expression system in *E. coli* [Wood, C. R. et al., (1990) J. Immunol., 145, 3011]. A library which expresses exact antigen-binding activity of the original antibody could be prepared, and the nucleotide sequence of variable region of antigen specific antibody could be screened effectively from the library. Natural human antibody is preferable for antibody therapeutics in view of antigenicity in human. A process for production of human antibody by means of recombinant DNA technology in use of animal host cells is preferable.

On the point that the final expression is performed by animal cells, use of animal cells at the screening step may be preferable, in order not to make difference in antigen-binding activity of antibody in the screening steps and the production steps.

As clearly explained hereinabove, although the screening system in *E. coli* for nucleotide sequence of variable region of antigen-specific H- and L-chain is known, development on more preferable screening system in use of eukaryotic cells, specifically animal cells is expected.

SUMMARY OF THE INVENTION

The present invention relates to a method for screening nucleotide sequence of variable region of antigen-specific antibody in use of eukaryotic cells, specifically animal cells, which are preferable for expression of antibody, and a vector therefor.

The inventors of the present invention have tried to find out the idea comprising preparing a vector which expresses antibodies on cell membrane, inserting nucleotide sequence of variable region of various antibody to the vector to express the antibodies on the cell membrane, concentrating the cells which express the antibodies binding to antigen in use of marker of antigen-binding activity, and obtaining the nucleotide sequence of variable region of antigen-specific antibody.

The present invention consists of the following concepts.

(1) An expression vector for preparing a library of an antibody variable region, which can express polypeptides containing the H-chain and/or L-chain variable regions of antibodies in the membrane-bound form on the surfaces of eukaryotic cells, and which is containing the nucleotide sequence of AKL (formula 1) and AKH (formula 2) and replicable in the cells:

$$5'\text{-}P_L\text{-}S_L\text{-}C_L\text{-}M_L\text{-}A_L\text{-}3' \quad \text{(formula 1)(AKL)}$$

$$5'\text{-}P_H\text{-}S_H\text{-}C_H\text{-}M_H\text{-}A_H\text{-}3' \quad \text{(formula 2)(AKH)}$$

wherein $P_L$ and $P_H$ represent a promoter, respectively; $S_L$ and $S_H$ represent a nucleotide sequence coding for a signal peptide, respectively; $C_L$ represents a nucleotide sequence coding for the L-chain constant region of an antibody; $C_H$ represents a nucleotide sequence coding for the H-chain constant region of an antibody or a nucleotide sequence coding for a polypeptide containing at least CH1 of the H-chain constant region of an antibody; $A_L$ and $A_H$ represent a polyadenylation signal, respectively; "5'-" and "-3'" refer to the 5' side and the 3' side, respectively, of the nucleotide sequence; and $M_L$ and $M_H$ represent a nucleotide sequence coding for the transmembrane domain, respectively while either $M_L$ or $M_H$ may be a mere chemical bond when the expression vector contains the nucleotide sequence of AKL and AKH. Cloning site of $R1_L$, $R2_L$, $R1_H$ and $R2_H$ is present within or in the vicinity of $S_L$, $C_L$, $S_H$ and $C_H$, respectively, in order for the nucleotide sequences coding for the L-chain and H-chain variable regions to be readily inserted in between $S_L$ and $C_L$, and $S_H$ and $C_H$, respectively.

(2) The expression vector according to the above (1) wherein the said cloning site of $R1_L$, $R2_L$, $R1_H$ and $R2_H$ is selected from recognition sequence of restriction enzymes [MunI, AclI, BspLU11I, MluI, BssHII, NheI, XbaI, SplI, Bspl407I, ClaI, XhoI, SalI and Afl II].

(3) The expression vector according to (1) wherein the said nucleotide sequence coding for the transmembrane domain of $M_L$ and $M_H$ is a nucleotide sequence coding for the transmembrane domain of thrombomodulin.

(4) The expression vector according to (3) wherein the said expression vector contains the nucleotide sequence of AKL and AKH, and the cloning site of $R1_L$, $R2_L$, $R_{1H}$ and $R2_H$ is the recognition sequence of XhoI, SplI, ClaI and MluI, respectively, and $M_L$ is a mere-chemical bond.

(5) The expression vector according to (3) wherein the said expression vector contains the nucleotide sequence of AKL and AKH, and the cloning site of $R1_L$, $R2_L$, $R1_H$ and $R2_H$ is the recognition sequence of XhoI, SpeI, BamHI and EcoRI, respectively, and $M_L$ is a mere chemical bond.

(6) The expression vector according to (3) wherein the said expression vector contains the nucleotide sequence of AKL and AKH, and the cloning site of $R1_L$, $R2_L$, $R1_H$ and $R2_H$ is the recognition sequence of XhoI, SpeI, BamHI and ApaI, respectively, and $M_L$ is a mere chemical bond.

(7) The expression vector according to (1) wherein the said vector is replicable in COS cells.

(8) A vector, which is used for preparing a library of antibody variable region, being inserted a large number of nucleotide sequences coding for H-chain variable regions of antibodies and/or nucleotide sequences coding for L-chain variable regions of antibodies into the cloning sites of the expression vector of (1).

(9) A group of eukaryotic cells comprising being expressed polypeptides containing the H-chain and L-chain variable regions of antibodies in the membrane-bound form on the surface of the cells by introducing the vectors containing the vector of (8) to the host cells.

(10) A method for selecting nucleotide sequences coding for antibody variable regions binding to a specific antigen from the nucleotide sequences coding for a large number of antibody variable regions, comprising:
  (a) isolating the cells bound to said antigen from the group of eukaryotic cells of (9), and
  (b) recovering the expression vector from the isolated cells to obtain nucleotide sequences coding for antibody variable regions bound to the antigen.

(11) The method according to (10) comprising immobilizing the antigen on the surface of the solid, and isolating the cells by adhering the cells, which express the antigen-binding polypeptide, to the immobilized antigen.

(12) The method according to (10) comprising labelling the antigen with fluorescent substance, biotin or magnetic beads and isolating the cells which express the antigen-binding polypeptide by flow cytometry or immunomagnetic beads method.

(13) A screening kit for nucleotide sequences coding for variable regions of the antigen-specific antibody comprising the expression vector of (1) or (8), host cells and auxiliary components.

As illustrated in a schematic representation of IgG1 in FIG. 1, antibody consists of two large and small polypeptides which are designated as "H-chain" for the large chain and "L-chain" for the small one. Each chain consists of a "variable region" for antigen-binding site in N-terminal region, and the fixed "constant region" depending upon the antibody classes. The constant region in H-chain consists of four domains and a domain in the N-terminal end is designated as "CH1".

"Promoter $P_L$ and $P_H$" and "nucleotide sequences $S_L$ and $S_H$ coding for signal peptide" in FIG. 1 and FIG. 2 are workable in eukaryote.

"The transmembrane domain" in the present invention means the transmembrane domain consisting of 15–30 amino acids abundant in hydrophobic amino acids and a region having anchor region consisting of charged amino acids in carboxyl terminus for positioning the carboxyl terminus to the cytoplasmic region. The "membrane-bound form" in the present invention means that antibodies have a transmembrane domain in the part of the antibodies.

A term "replicable in the cells" in the present invention means that the vector can be autoreplicable independently from the host chromosome when it is transduced into prokaryotic cells such as *E. coli* or eukaryotic cells such as animal cells. To be more concrete, the autoreplication in *E. coli* can be achieved by recombinating the ori from pBR322 or pUC18 in the vector, or autoreplication in COS cells can be performed by recombinating the ori from SV40 in the vector.

A term "mere chemical bond" means phosphodiester bond binding 5'-carbon in deoxyribose of a nucleotide to 3'-carbon in deoxyribose of the next nucleotide. "COS cells" includes COS1 cell (ATCC CRL 1650) and COS7 cell (ATCC CRL 1651). A term "auxiliary components" includes *E. coli* for host cell, and reagents and buffer solution used for reactions such as restriction enzyme digestion, DNA ligation, gene transduction and antigen labelling. Antibody is a tetrameric protein composed of two heavy (H) chains and two light (L) chains of peptides (refer to FIG. 1). Each chain consists of a variable region which makes up the antigen-binding site and a constant region which determines the immunoglobulin class to which the molecule belongs. Antigen specificity of antibody is determined by combination of H-chain and L-chain variable regions. Genetic engineering process for preparation of antigen specific antibody requires at least H-chain and L-chain variable region nucleotide sequence of antigen specific antibody.

Consequently, an object of the present invention is to provide a screening method for nucleotide sequence of variable region of antigen-specific antibody in use of expression system of eukaryotic cells, specifically animal cells.

We have found that a method for obtaining nucleotide sequence of variable region of antigen-specific antibody comprising expressing antibodies on the host cell membrane, and selecting and isolating the host cells which express antigen-specific antibodies by means of antigen-binding activity of the antibodies which are expressed on the membrane.

Antibodies consist of secretory type and membrane-bound type, the latter of which is expressed on the cell membrane as a B cell receptor and which is known to require the other subunit depending on its class for expression on the membrane [Venkitaraman, A. K. et al., (1991), Nature, 352, 777]. We have had an idea that the constant region of the antibodies was made in secretory type for possible expression of the antibodies per se, and the transmembrane domain of the membrane protein other than antibody was linked to carboxyl terminus of H-chain and/or L-chain of the antibodies for expressing the antibodies on the cell membrane.

In case that any one of a nucleotide sequence of AKL of the formula 1 and AKH of the formula 2 is integrated in the vector, the chain, which is not integrated therein (for example, H-chain in case of AKL in the vector, and L-chain in case of AKH in the vector), is previously incorporated in the host cells, or should be integrated in the host cells by cotransduction of the other vector containing the chain.

Preparation of plasmid vector pSEL, an example of a vector which expresses antibodies on the cell membrane, is illustrated in Example 1. Plasmid vector pSEL has been deposited in National Institute of Bioscience and Human-Technology, Agency of Industrial Science and Technology, Ministry of International Trade and Industry, as deposition *E. coli*: JM109-pSEL (FERM BP-4896) on Nov. 18, 1994.

In the pSEL, human IgG1 constant region nucleotide sequence (Cγ1) for a nucleotide sequence coding for H-chain constant region (hereinafter designates as constant region nucleotide sequence), human κ chain constant region nucleotide sequence (Cκ) for L-chain constant region nucleotide sequence, and transmembrane domain nucleotide sequence of human thrombomodulin (TM) are inserted and TM is ligated at 3' terminus of Cγ1. Cloning sites are constructed for 5' terminus of H-chain variable region nucleotide sequence by introducing BamHI site in one side, and for 3' termions of the H-chain variable region nucleotide sequence in use of the originally located ApaI site at the neighbouring with 5' terminus of Cγ1 in the other side. In the L-chain, XhoI site is newly introduced at 5' terminus and, for 3' terminus, SpeI site is newly introduced in the neighbouring with 5' terminus of Cκ. Genes of H-chain and L-chain are located at down stream of each promoter and arranged in tandem for the same direction. The pSEL contains ori from pBR322 for autoreplication in *E. coli*, and ori from SV40 for autoreplication in COS cells.

Examples of vectors which express the antibodies on cell membrane are illustrated in Examples 2 and 3 for preparation of plasmid vector pSE and plasmid vector pSE 2. The plasmid vector pSE has been deposited in National Institute of Bioscience and Human-Technology, Agency of Industrial Science and Technology, Ministry of International Trade and Industry as deposition *E. coli*: JM109-pSE (FERM BP-4894), and the plasmid vector pSE2 has been deposited in the same institution as deposition *E. coli*: JM109-pSE2 (FERM BP-4895) on Nov. 18, 1994.

The plasmid vector pSE is basically the equivalent vector to pSEL except the original vector is pUC18, and ApaI cloning site in pSEL is replaced by EcoRI cloning site. In pSE2, cloning sites are replaced as follows:

BamHI→ClaI, EcoRI→MluI and SpeI→SplI.

Primary condition on a restriction enzyme at cloning site for cloning nucleotide sequence of human antibody variable region is that the recognition sites of the restriction enzyme should not be located at least in human germ line $V_H$, D, $J_H$ and $J_L$ genes. Hitherto reported human germ line $V_H$, D, $J_H$ and $J_L$ genes were searched in the references [SEQUENCES OF PROTEINS OF IMMUNOLOGICAL INTEREST FIFTH EDITION (1991), U.S. Department of Health and Human Services, Public Health Service National Institutes of Health; Schable, K. F. et al. (1993) Biol. Chem. Hoppe-Seyler, 374, 1001, Williams, S. C. et al. (1993) Eur. J. Immunol., 23, 1456; Matsuda, F. et al.(1993) Nature Genetics, 3, 88; Cook, G. P. et al. (1993) Nature Genetics, 7, 162] and the data base (GenBank and EMBL), and restriction sites were retrieved. The recognition sites of restriction enzymes such as MunI, AclI, BspLU11I, MluI, BssHII, NheI, XbaI, SplI, Bspl407I, ClaI, XhoI, SalI and Afl II were not found to exist in the known human germ line $V_H$, D, $J_H$, $V_L$ and $J_L$ genes. Consequently, these recognition sites of the enzyme can be used as cloning sites. Cloning site for pSE2 is selected from the above commercially available enzymes.

Separation of the nucleotide sequence of variable region is performed by PCR (polymerase chain reaction). Amplification and separation of nucleotide sequences of variable region of antibodies by PCR have been known [Orlandi, R. et al. (1989), Proc. Natl. Acad. Sci. USA, 86, 3833]. Preparation of nucleotide sequence of variable region of mouse monoclonal antibody M21 for rat IgG2b and expression thereof in COS7 cells are illustrated in Example 4.

Examples of primers for amplification of nucleotide sequences of mouse H-chain variable region are shown in Table 1. Examples of primers for amplification of nucleotide sequences of mouse κ chain variable region are shown in Table 2.

Variable region of antibody is composed of framework region and hypervariable region, and is classified into subgroups according to homology of amino acid sequence in the framework region [SEQUENCES OF PROTEINS OF IMMUNOLOGICAL INTEREST FIFTH EDITION (1991), U.S. Department of Health and Human Services, Public Health Service National Institutes of Health].

Conserved sequence located at 5' terminus of the variable region in the subgroup is used as a reverse primer. Complementary strand nucleotide sequence from 3' terminus of mouse $J_H$ and $J_K$ genes to 5' terminus of $C\gamma_1$ and $C\kappa$ is used as a forward primer. The reverse primer sequence and the forward primer sequence in H-chain variable region have BamHI site and ApaI site, respectively. The reverse primer sequence and the forward primer sequence in L-chain variable region have XhoI site and SpeI site, respectively. PCR product of H-chain variable region and pSEL are digested by BamHI and ApaI and ligated to insert nucleotide sequence of the H-chain variable region into pSEL. Similarly, PCR product of L-chain variable region and pSEL are digested by XhoI and SpeI, and ligated to insert nucleotide sequence of the L-chain variable region into pSEL.

Preparation of a library of antibody variable region is exemplified in Example 5. Nucleotide sequences of the variable region are amplified and separated by PCR from various antibody-producing cells, and the library of the antibody variable region is prepared by inserting them in pSEL as shown in Example 4. Since nucleotide sequences of H-chain and L-chain variable region are isolated independently thereafter combined on the plasmid, antibody repertoire which has not been existed in vivo is possibly incorporated in the library.

Selection of nucleotide sequences of antibody variable region having the antigen sepcificiy is illustrated in Example 6. Vector DNA of the library to be selected is introduced into host cells by electroporation, DEAE dextran method and others. In Example 6, the electroporation is applied. Electroporation is described in the experimental books (Series Biochemical Experiments 1, Methods in Research Studies on Genes III, Chapter 15, Electroporation, Igarashi, T. et al.). On two to three days culture aftertransduction of the vector DNA, the antibodies are expressed on the host cell membrane. The host cells which express antigen-binding antibodies on the membrane are separated by means of indicator of antigen-binding activity. Examples of separation methods are a panning method in which antibody expression cells are plated on the surface of antigen-bound plastic plate and the cells expressed antigen-binding antibody on the surface are adhered and separated, and a cell sorting method by flow cytometry in which antigen-binding antibody expressed cells are specifically stained by an antigen previously labelled with fluorescent FITC or biotin. The panning method is described in "Biomanual Series 3, Gene Cloning" [Yokota, T. and Arai, K. Ed. (1994). Yodosha Publ.]. The sorting method is described in "Flow cytometry-Technique and Practice" [Ed. Ota, K. and Nomura, K. (1984), Kani Publ. Co.]. Vector DNA is recovered from separated host cells by means of Hirt method [Hirt, B. (1967), J. Mol. Biol., 26, 365]. A procedure of the above concentration operation is repeated for several processes to obtain nucleotide sequence of antigen-specific antibody variable region. In Example 6, one operation results in 54-fold concentration, however superior effective concentration could be achieved by the improvement of the conditions, such as sorting conditions.

Hereinabove exemplified processes are illustrations of a model system in use of mouse monoclonal antibody M21 and its antigen rat IgG2b anti L3T4 antibody GK1.5. Examples 7 and 8 hereinbelow are exemplified by showing a preparation of a library of human antibody variable region in use of pSE plasmid, and experimental data of screening of human anti-HBs antibody.

In Example 7, peripheral blood lymphocytes of volunteer who is anti-HBs antibody positive are used as a gene source. Human antibody variable region nucleotide sequences are isolated by PCR and inserted in a plasmid pSE to prepare a library of human antibody variable region composed of approximately $5 \times 10^6$ colonies. Examples of primer for nucleotide suquences of human H-chain variable region are shown in Table 4 and those for nucleotide sequences of human κ chain variable region are shown in Table 5.

Variable region of antibody is composed of framework region and hypervariable region, and is classified into subgroups according to homology of amino acid sequence in the framework region [SEQUENCES OF PROTEINS OF IMMUNOLOGICAL INTEREST FIFTH EDITION (1991). U.S. Department of Health and Human Services, Public Health Service National Institutes of Health].

Conserved sequence located at 5' terminus of the variable region in the subgroup is used as a H-chain reverse primer. Complementary strand nucleotide sequence of 3' terminus of human $J_H$ gene is used as a H-chain forward primer. A complementary strand nucleotide sequence from 3' terminus of $J_K$ gene to 5' terminus of Cκ gene is used as a L-chain forward primer. The reverse primer sequence and the forward primer sequence in H-chain variable region have BamHI site and EcoRI site, respectively. The reverse primer sequence and the forward primer sequence in L-chain variable region have XhoI site and SpeI site, respectively. PCR product of H-chain variable region and pSE are digested by BamHI and EcoRI, and ligated to insert nucleotide sequence of the H-chain variable region into pSE. Similarly, PCR product of L-chain variable region and pSE are digested by XhoI and SpeI, and ligated to insert nucleotide sequence of the L-chain variable region into pSE.

In Example 8, clones bound with recombinant HBs antigen are isolated by starting from approximately $3 \times 10^7$ COS7 cells from the library, and concentrating three times with biotin-labelled recombinant HBs antigen. Nucleotide sequences of H-chain variable region and κ chain variable region are obtained from the thus obtained clones, and are, for example, introduced into COS cells after inserting those sequences into secretory antibody-producing vector in which TM site is removed from pSE plasmid in FIG. 4 to prepare human anti-HBs monoclonal antibody by well known method [Xiang, J. et al. (1990), Mol. Immun., 27, 809; Bebbington, C. R. et al. (1992), Bio/technology, 10, 169].

As explained hereinabove, nucleotide sequences of variable region in antigen-specific antibody can be screened by a method of the present invention in case of animals such as mouse and human wherein detailed informations on nucleotide sequence of antibody variable region are available. These screenings can easily be performed by use of the screening kit consisting of the expression vectors, host cells and auxilary components necessary for operating the present invention.

BRIEF EXPLANATION OF THE DRAWINGS

FIG. 3, 1) shows staining with goat anti-human immunoglobulin antibody. Horizontal axis indicates amount of human immunoglobulin expressed on COS7 cells. About 35% of COS7 cells express M21 chimera antibody.

FIG. 3, 2) shows antigen (GK1.5)-binding activity of the expressed M21 chimera antibody. About 35% of COS7 cells show GK1.5-binding activity, from which the expressed M21 chimera antibody has binding activity for antigen GK1.5.

DETAILED DESCRIPTION OF THE PREFERRED EMBODIMENTS

Following examples illustrate the present invention but are not construed as limiting.

EXAMPLE 1

(Preparation of pBR322 series membrane binding antibody expression plasmid pSEL)

Human Cγ1 gene, to which a nucleotide sequence coding for human H-chain signal sequence at 5' terminus and nucleotide sequence coding for transmembrane domain of human thrombomodulin at 3' terminus were ligated, was inserted into a plasmid pSR, 3.1 kb, having ori from SV40, SRα promoter, polyadenylation signal and cloning sites of HindIII and XbaI, originated from pBR322 to construct a plasmid pSR-GM (4.7 kb). ApaI site located in the neighbouring with 5' terminus of Cγ1 was used for cloning site in the 3' terminus of H-chain variable region nucleotide sequence. BamHI site was introduced in the 5' terminus of H-chain variable region nucleotide sequence. Introduction of BamHI site was performed by the following process. HindIII site and BamHI site were introduced in the 5' terminus and 3' terminus, respectively, of nucleotide sequence coding for the region from H-chain signal peptide to N-terminal of H-chain variable region to synthesize the nucleotide fragment. The fragment was then temporarily inserted in the plasmid DNA in which Cγ1 and TM were previously inserted. A DNA fragment containing H-chain signal peptide, Cγ1 and TM, in this order, was obtained by cutting at HindIII site and XbaI site located in the 3' side of TM. The thus obtained DNA fragment was inserted in pSR which was cut at HindIII site and XbaI site (pSR-GM).

Figure 1:
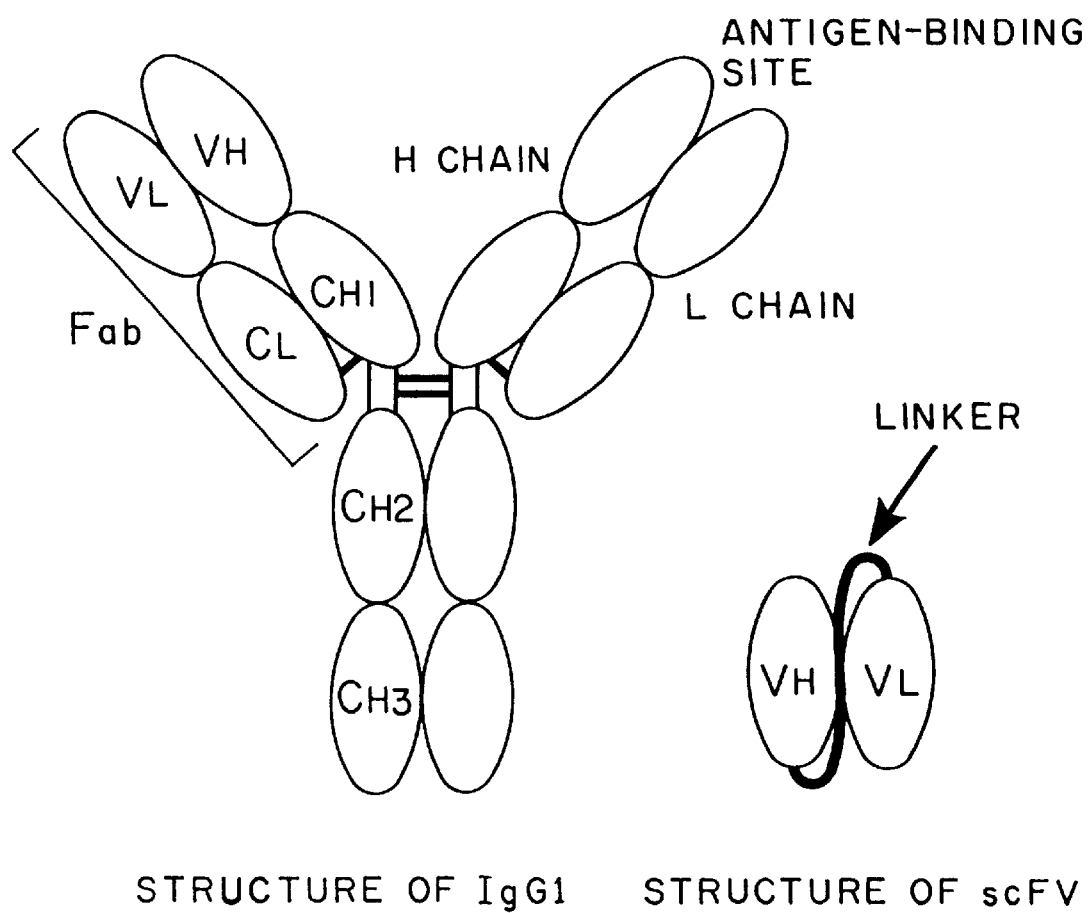
FIG. 1 shows schematic representation of IgGI and scFv wherein Fab is composed of L-chain, and VH and CH1 domains, and scFv consists of VH domain and VL domain which are linked by linker.
Figure 2:
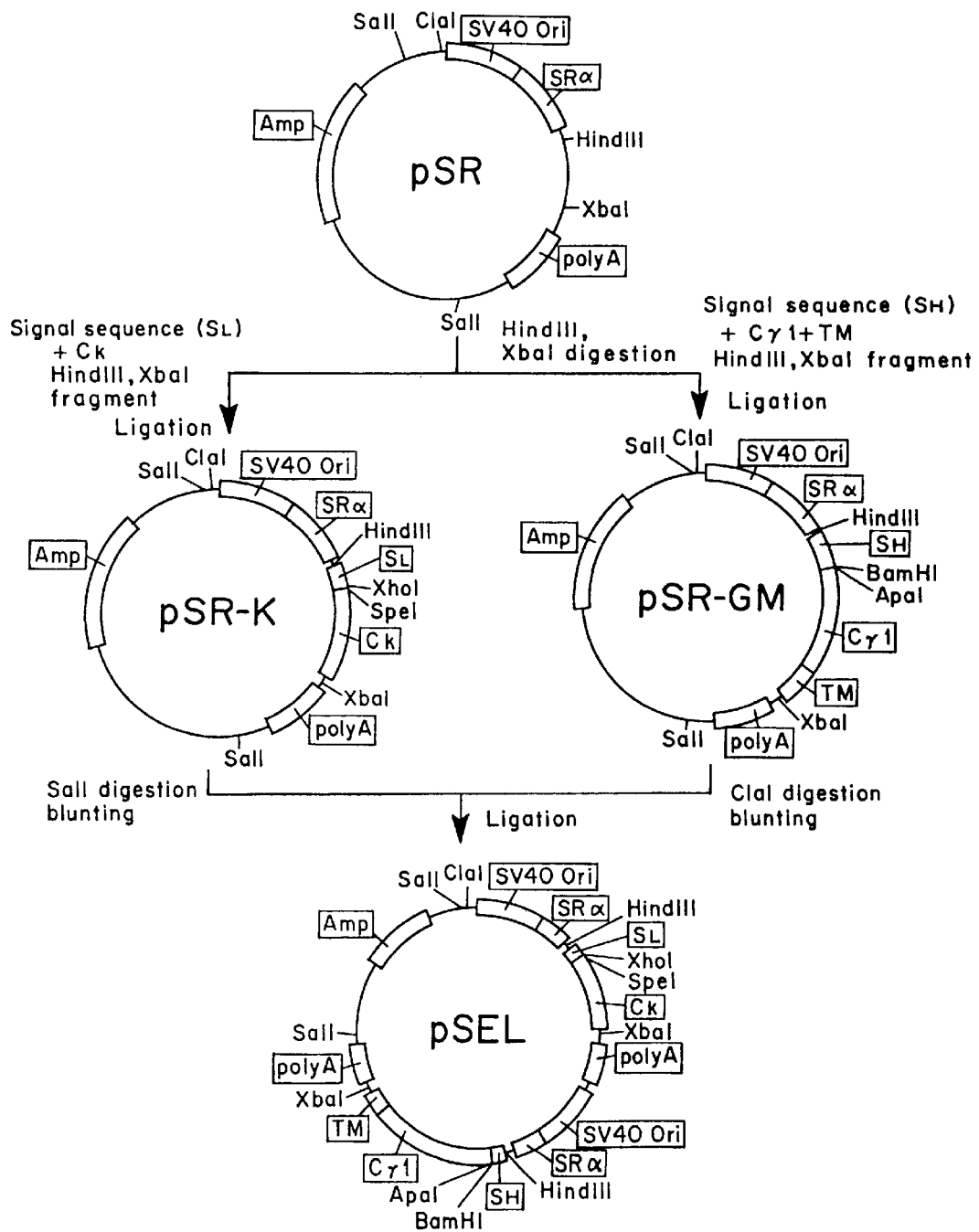
FIG. 2 shows illustration of pSEL preparation process.

Similarly, a plasmid pSR-K (3.9 kb) was constructed by inserting a nucleotide sequence coding for human κ chain signal sequence and human Cκ gene in pSR. Cloning site was constructed by newly inserting XhoI site in the 5' terminus and SpeI site at the neighbouring of 5' terminus of Cκ in the 3' terminus. For introduction of cloning site, HindIII site and XhoI site were introduced in the 5' terminus and 3' terminus, respectively, of the nucleotide sequence coding for the region from L-chain signal peptide to N-terminal of L-chain variable region to synthesize the nucleotide fragment. The thus totally synthesized nucleotide fragment was temporarily inserted in the plasmid DNA. Cκ, for which SpeI site had been introduced by mutation, was previously incorporated in the said DNA. DNA fragment containing L-chain signal peptide and Cκ was cut at the HindIII site and the XbaI site in the 3' side of Cκ, and was inserted in pSR which was cut at HindIII and XbaI sites (pSR-K). The pSR-K was digested by SalI (Takara Shuzo Co. hereinafter designates as Takara). After preparing blunt end by treating with a commercially available kit (DNA blunting kit, Takara), a fragment, 2.0 kb, containing Cκ gene was isolated and extracted by agarose gel electrophoresis. The fragment was digested with ClaI (Takara) and ligated with pSR-GM to prepare pSEL. (FIG. 2)

EXAMPLE 2

(Preparation of pUC18 sesries membrane binding antibody expression plasmid pSE)

A plasmid pEN-GM (5.3 kb) was prepared by inserting a HindIII-XbaI fragment containing human Cγ1 gene in pSR-GM, 1.6 kb into the HindIII and XbaI cloning sites of a plasmid pEN, 3.7 kb, originated from pUC18, having ori from SV40, SRα promoter and polyadenylation signal. A plasmid pEN-K (4.5 kb) was prepared by inserting a HindIII-XbaI fragment (0.8 kb) containing human Cκ gene of pSR-K in pEN.

Figure 4:
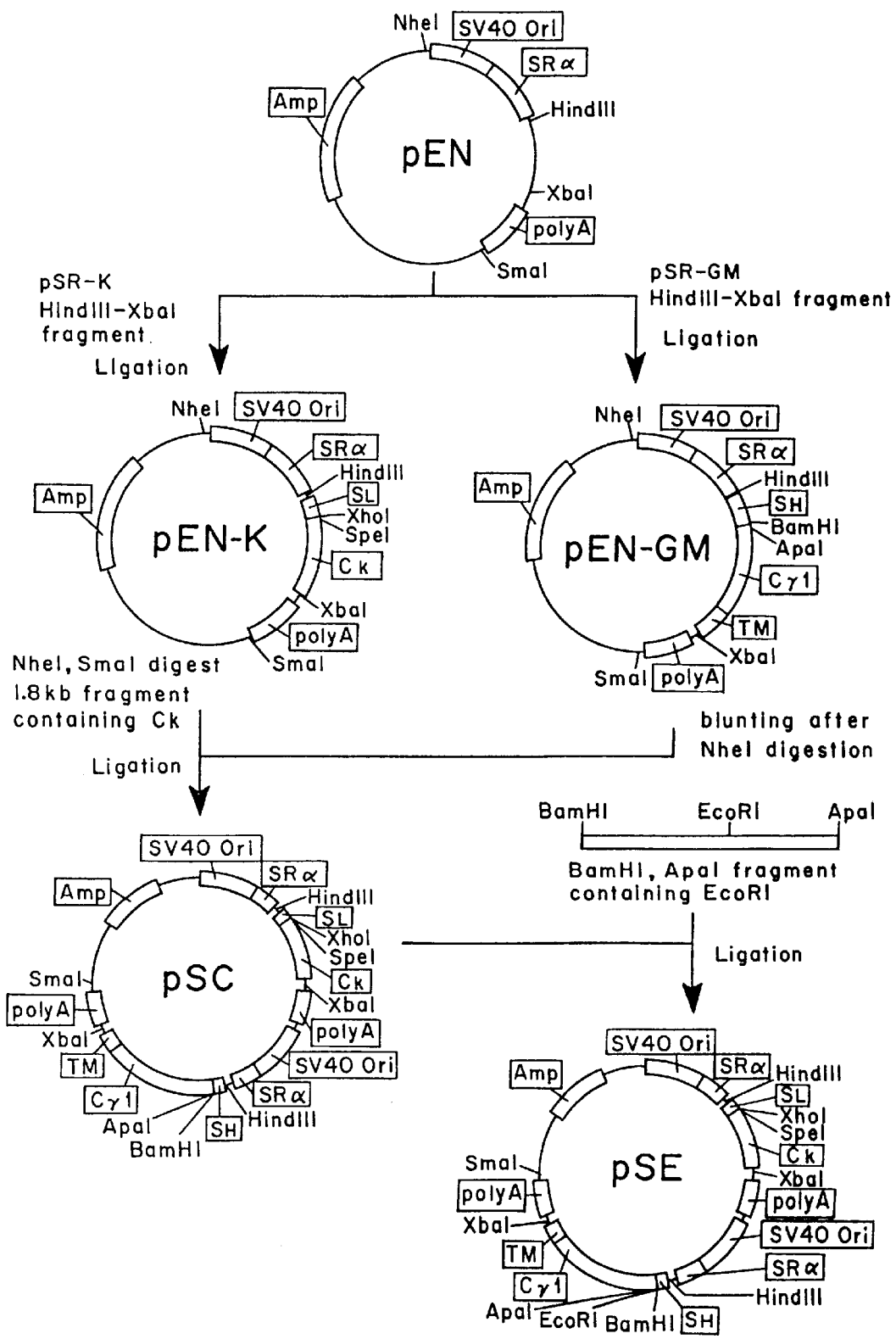
FIG. 4 shows an illustration for production of pSE.

The pEN-K was digested by NheI (Takara) and SmaI (Takara) to prepare blunt end, and a fragment (1.8 kb) containing Cκ gene was separated and extracted by agarose gel electrophoresis. The fragment was ligated with pEN-GM which was digested by NheI and blunt-ended. The plasmid pSC in which direction of transcription of Cκ gene was identical with that of Cγ1 gene, was selected from the thus prepared plasmid. For introducing new EcoRI site in the downstream region between the two cloning sites of H-chain variable region of pSC, a fragmnet within BamHI-ApaI in pSR-GM was amplified by PCR in use of a primer 1 (5'-GTCCCAGGATCCCCGG-3') (SEQ ID NO:1) and a primer 2 (5'-CCGATGGGCCCTTGGTGGAGGCTGAATTCACG GTGACCGTGGTCC-3') (SEQ ID NO:2). PCR was performed by the conditions at 94° C. for 1 min.→at 55° C. for 2 min.→at 72° C. for 2 min. in 25 cycles. The thus obtained amplified fragments were digested with BamHI (Takara) and ApaI (Takara) and inserted into pSC in place of the BamHI-ApaI sequence in pSC. Newly prepared plasmid having the cloning site of BamHI and EcoRI in H-chain variable region is designated as pSE. (FIG. 4)

EXAMPLE 3

(Preparation of pSE2 by modification of pSE)

A plasmid was prepared by changing BamHI and EcoRI of cloning sites in H-chain variable region of pSE to ClaI and MluI sites, and introducing SplI site in a boundary between L-chain variable region and Cκ gene as a downstream cloning side of L-chain variable region.

In order to replace the cloning site of H-chain variable region nucleotide sequence, a HindIII-ApaI fragment, approximately 80 bp, containing H-chain signal sequence of pSE was amplified by PCR in use of a primer HS (5'-TTTTAAGCTTGAACATGAAACACCTGTGGTT-3') (SEQ ID NO:3) and a primer HC (5'-CGATGGGCCCTTGGTGGGAGGCT-GACGCGTTATAATCGATTGGGACAGGAC-CCTGACATCTGGGAGC TG-31') (SEQ ID NO:4). Condition of PCR was at 94° C. for 1 min.→at 65° C. for 1 min.→at 72° C. for 1 min. in 25 cycles. The thus obtained amplified fragments were digested by HindIII and ApaI. The digested fragment was replaced by the sequence between HindIII-ApaI sites in pSE to prepare a plasmid pSE-CM having cloning sites of ClaI and MluI.

Figure 5:
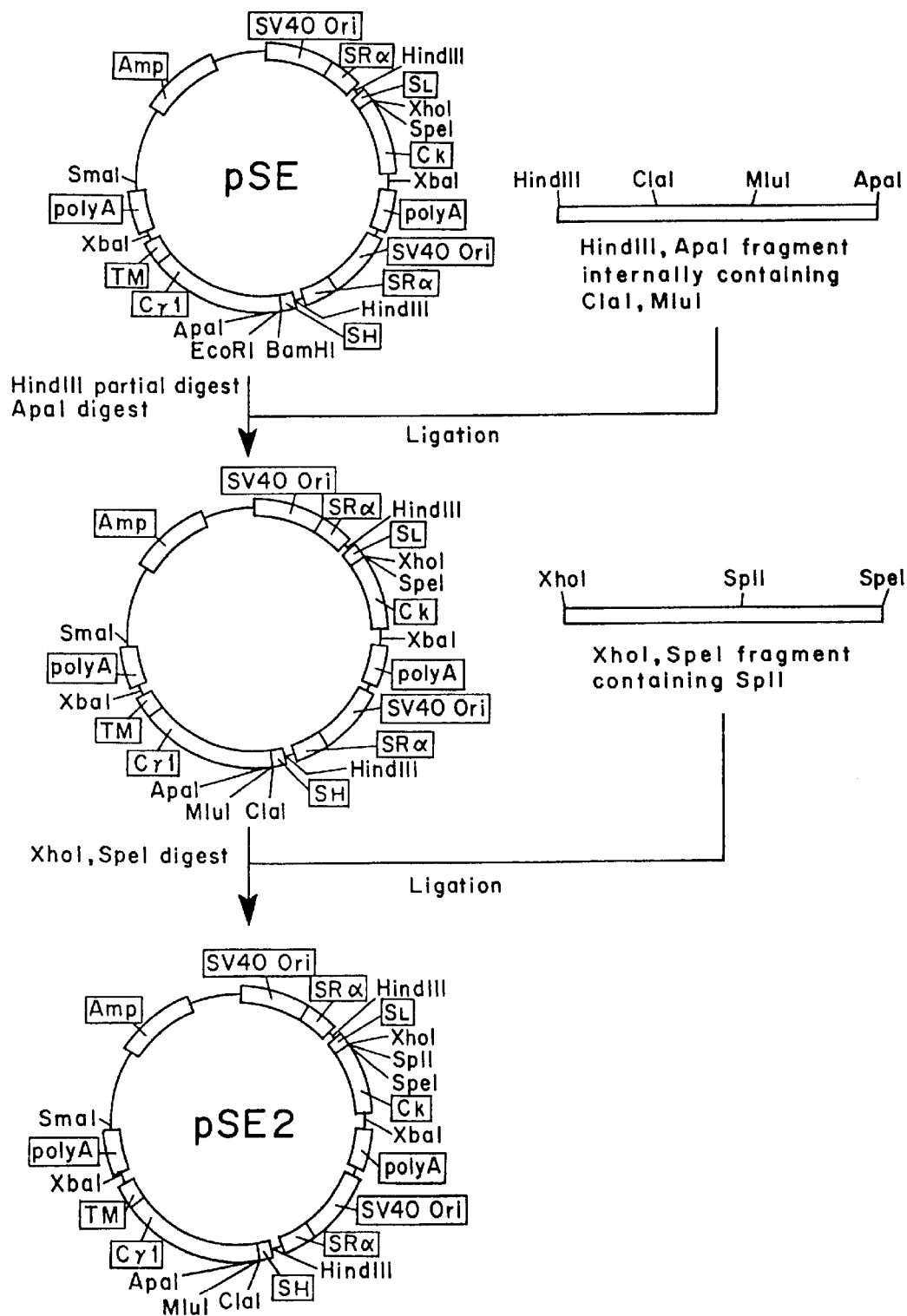
FIG. 5 shows an illustration for production of pSE2.

SpII site was newly introduced in use of synthetic oligonucleotide LS (5'-TCGAGAATTCGTACGGTGGCTGCACCA-3') (SEQ ID NO:5) and LC (5'-CTAGTGGTGCAGCCACCGTACGAATTC-3') (SEQ ID NO:6). A mixture of equivalent amount of aqueous solution of LS and LC (1 mg/ml) in a tube was immersed in water. After boiling the water, LS and LC were annealed by slightly cooling with standing at room temperature for about 3 hours. The thus generated LSLC mixture and pSE-CM treated with XhoI and SpeI digestion were mixed at a molar ratio of 3:1 to ligate. Ligation Kit Ver. 2 (Takara) was used for the ligation. The new plasmid having SpII site is designated as pSE2. (FIG. 5)

EXAMPLE 4
(Expression of M21 mouse monoclonal antibody on COS7 cells)

Mouse monoclonal antibody M21 (IgG1κ) is an antibody for rat IgG2b. A cDNA was synthesized from mRNA extracted from M21 hybridoma. H-chain and κ chain variable region fragments of M21 were cloned by PCR in use of the cDNA as a template. Extraction of mRNA was performed in use of Quick Prep mRNA purification Kit (Pharmacia Inc.). The cDNA synthesis was performed by cDNA Synthesis Kit (Boehringer Mannheim A.G.). These are commercially available kits and the procedures were performed according to the attached protocol.

Primers used for PCR amplification of H-chain variable region are shown in Table 1 and primers used for that of κ chain variable region are shown in Table 2. PCR was performed in use of GeneAmp PCR Reagent Kit with AmpliTaq DNA Polymerase (Takara) and was conducted at 94° C. for 1 min.→at 55° C. for 2 min.→at 72° C. for 2 min. in 35 cycles, in 1.0–2.0 mM $Mg^{2+}$. Result of PCR indicated that $V_H$ and $V_K$ genes of M21 were supposed to belong to subgroups I(B) and III, respectively. PCR product of H-chain variable region was digested by BamHI and ApaI and inserted into pSEL to prepare pSELM21VH. PCR product of κ chain variable region was digested by XhoI (Takara) and SpeI (Takara) and inserted into pSELM21VH to construct membrane-bound M21 chimera antibody expression vector pSELM21.

Plasmid DNA of pSELM21 was transferred to COS7 cells by means of electroporation. Expression of M21 chimera antibody on COS7 cells was analyzed by flow cytometry. Gene transfer by electroporation was performed in use of Gene Pulser (Bio-Rad Corp.) as follows. Subcultured COS7 cells with DMEM containing 10% FCS (GIBCO BRL Inc.) were inoculated, $3\times10^6$ cells/plate, into a dish, diameter 150 mm, on the day before gene transfer. Cultured COS7 cells were washed twice with 15 ml of PBS (−)(Flow Laboratories Inc.) and harvested from dish by adding 5 ml of EDTA trypsin solution (CosmoBio Inc.). Trypsin was inactivated by adding 3 ml of DME containing 10% FCS.

Cells were washed twice with 10 ml of previously cooled PS buffer solution (272 mM sucrose, 1 mM $MgCl_2$ and 7 mM sodium phosphate pH 7.4), and suspended at $8\times10^6$ cells/ml in PS buffer solution. 0.5 ml of cell suspension was set in Gene Pulser Cuvette (0.4 cm), and 5 μl of plasmid DNA (4 μg/ml distilled water) was added thereto and stirred. After set on ice for 5 minutes, the cells were twice pulsed at 3 μF. 500 V with 30 sec. intervals. Further cells were set on the ice for 5 min., transferred into dish, diameter 100 mm, and cultured in 10 ml of DMEM containing 10% FCS at 37° C. Temperature of the culture was set at 33° C. after 4 hours. Culture medium was exchanged on the next day to remove dead cells and cultured for 60–72 hours. Cells were washed twice with 5 ml of PBS (−). Previously ice-cooled 4 ml of 0.02% EDTA-PBS (−) were added in the dish, stood for 15 minutes at 4° C. and released cells were recovered. Dish was washed with 1 ml 0.02% EDTA-PBS (−) and the washed solution was combined with the recovered cells for analysis.

Expression of M21 mouse chimera antibody on the pSELM21 transformed COS7 cells was determined. 50 μl of FITC-labelled goat anti-human immunoglobulin antibody (TAGO Inc: Cat. No. 2193), which was diluted 50-fold with PBS(−) containing 1% BSA and 20% goat serum, were added to the transformed cells and reacted for 30 minutes on the ice. Cells were spun down to remove supernatant, washed with 200 μl of 1% BSA-PBS(−) and further spun down to remove supernatant. This washing operation was repeated for 3 times. After washing, cells were suspended in 100 μl of PBS (−) to prepare a sample for flow cytometry.

Binding activity of the expressed chimera antibody to antigen GK 1.5 (rat IgG2b anti-mouse L3T4 antibody) was determined. 50 μl of biotin-labelled GK1.5, which was diluted 100-fold with 1% BSA-PBS (−), were added to the transformed cells $2\times10^5$ and reacted for 30 min. on the ice. Cells were spun down and washed three times. 50 μl of stock solution of PE-labelled streptoavidin (Biomeda Ind: Cat. No. P22), which was diluted tenfold with 1% BSA-PBS (−), were added to the cells and reacted for 30 min. on the ice. Cells were spun down and washed three times. Washed cells were suspended in 100 μl of PBS (−) to prepare a sample for flow cytometry.

Figure 3:
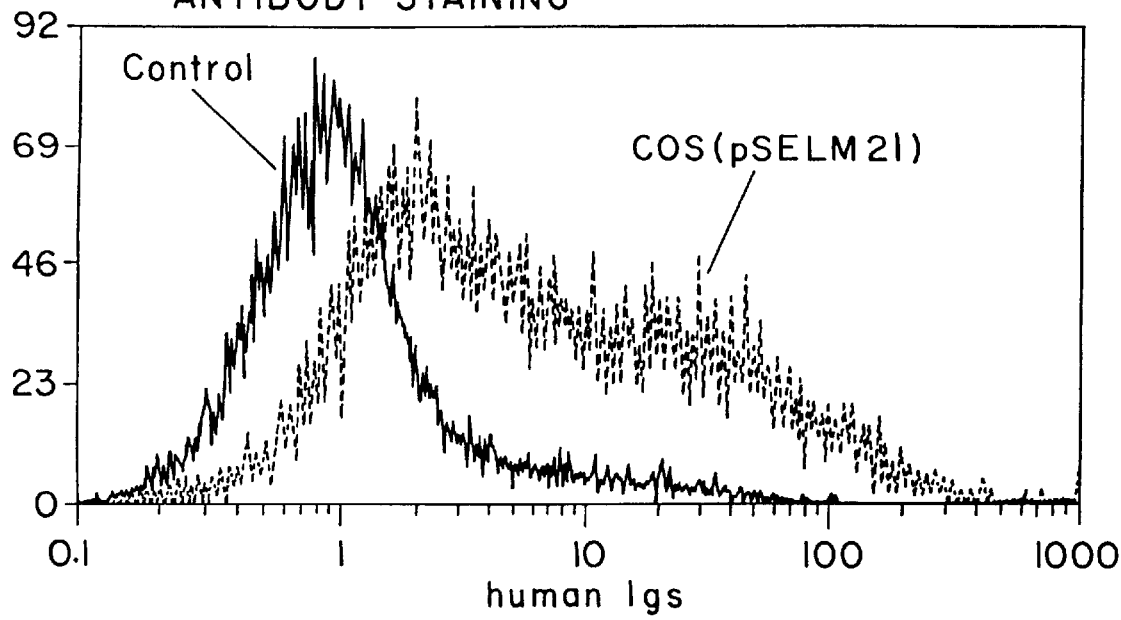
FIG. 3 shows flow cytometric analysis of an expression of M21 chimera antibody on COS7 cells. Control: COS7 cells without transformation of plasmid. COS(pSELM21): COS7 cells with transformation of pSELM21.
Figure 3:
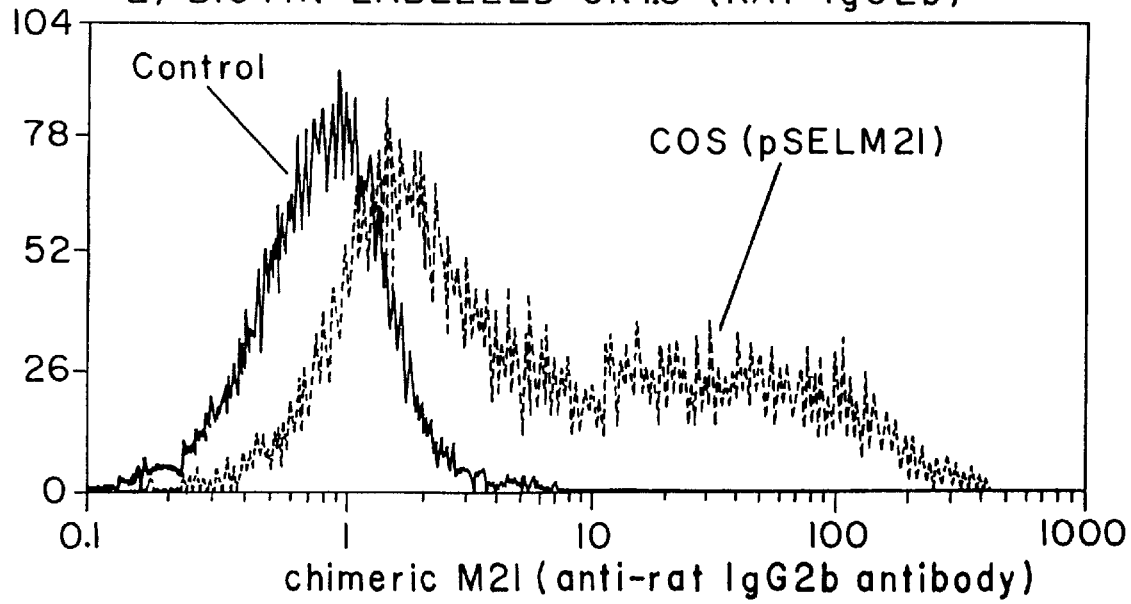

Flow cytometric analysis was performed in use of EPICS Elite (Coulter Inc.). Operation was performed according to the operational procedure. Result of flow cytometry is shown in FIG. 3. M21 chimera antibody was expressed on COS7 cells transformed with pSELM21. Also antigen (GK1.5) binding activity was maintained.

TABLE 1

Primer for amplifying mouse H-chain variable region nucleotide sequence

| Primer | Sequence | |
|---|---|---|
| 1) Reverse primer (a primer at 5' terminus: underline indicates BamHI site) | | |
| M-1A | GTCCCA<u>GGAT</u> <u>CCG</u>CTTCAGG AGTCAGGACC<br>           C        C    C C<br>                               G | SEQ ID NO: 7 |
| M-1B | GTCCCA<u>GGAT</u> <u>CCG</u>CTGAAGG AGTCAGGACC | SEQ ID NO: 8 |

TABLE 1-continued

Primer for amplifying mouse H-chain variable region nucleotide sequence

| Primer | Sequence | |
|---|---|---|
| | ```
          A    AC       T    C
        T
``` | |
| M-2A | ```
GTCCCAGGAT  CCGCTGCAAC  AATCTGGACC
            A  C TG     GC A  GC
``` | SEQ ID NO: 9 |
| M-2B | ```
GTCCCAGGAT  CCACTGCAGC  AGCCTGGGGC
            C  A  AG    AT     AA
            G  C                C
            T              T
``` | SEQ ID NO: 10 |
| M-3A | ```
GTCCCAGGAT  CCGCTGGTGG  AATCTGGAGG
            C   A        G     G
``` | SEQ ID NO: 11 |
| M-3B | ```
GTCCCAGGAT  CCGCTTCTCG  AGTCTGGAGG
            T  A  C        A
``` | SEQ ID NO: 12 |
| M-3C | ```
GTCCCAGGAT  CCGCTTGAGG  AGTCTGGAGG
             G TT        A   AG
``` | SEQ ID NO: 13 |
| M-3D | ```
GTCCCAGGAT  CCGCTGGTGG  AGTCTGGGGG
            CG A             A
            T  T
``` | SEQ ID NO: 14 |
| M-6 | ```
GTCCCAGGAT  CCGCTCGTGG  AGTCTGGGGG
             C  GT       A   CA
``` | SEQ ID NO: 15 |
| M-7 | ```
GTCCCAGGAT  CCGTTGGTAC  AGTCTGGACC
              G              T
``` | SEQ ID NO: 16 |

2) Forward primer (a primer at 3' terminus: underline indicates ApaI site)

| MG1-1 | ```
ACAGATGGGC  CCGTCGTTTT  GGCTGAGGAG  A
                           C
                           G
``` | SEQ ID NO: 17 |
| MG1-2 | ```
ACAGATGGGC  CCGTCGTTTT  GGCTGCAGAG  A
                           A
                           C
``` | SEQ ID NO: 18 |

TABLE 2

Primer for amplifying mouse κ chain variable region

| Primer | Sequence | |
|---|---|---|

1) Reverse primer (a primer at 5' terminus: underline indicates XhoI site SEQ ID NOS: 19—30)

| MK5-1 | ```
TGTGCCCTCG  AGATGACACA  GTCTCCATCC  T
              T  T        G   A A
                                T
``` | SEQ ID NO: 19 |
| MK5-2A | ```
TGTGCCCTCG  AGATGACCCA  AACTCCACTC  TC
              G   T      G  T       A
``` | SEQ ID NO: 20 |
| MK5-2B | ```
TGTGCCCTCG  AGATGACGCA  GGCTGCATTC  T
                T              CCC
``` | SEQ ID NO: 21 |
| MK5-2C | ```
TGTGCCCTCG  AGATAACCCA  GGATGAACTC  TC
              G G         A
                T
``` | SEQ ID NO: 22 |
| MK5-3 | ```
TGTGCCCTCG  AGCTGACCCA  ATCTCCAGCT
              A            G    T
``` | |
| MK5-4 | ```
TGTGCCCTCG  AGCTCACCCA  GTCTCCAGC
                               A
``` | |
| MK5-5A | ```
TGTGCCCTCG  AGATGACACA  GACTACATCC  TC
                           A
``` | |

TABLE 2-continued

Primer for amplifying mouse κ chain variable region

| Primer | Sequence |
|---|---|
| MK5-5B | TGTGCC<u>CTCG AGA</u>TGACACA GTCTCCATCC T<br>              A   C                        T |
| MK5-5C | TGTGCC<u>CTCG AGA</u>TGACTCA GTCTCCAGCC<br>              C A C                      T |
| MK5-5D | TGTGCC<u>CTCG AGA</u>TGACCCA GTCTCCCAAA TCC<br>                              AA   AA     T |
| MK5-5E | TGTGCC<u>CTCG AGG</u>TGACCCA GTCTCCAGCA |
| MK5-6  | TGTGCC<u>CTCG AGC</u>TCACCCA GTCTCCAGC<br>                  T T |

2) Forward primer (a primer at 3' terminus: underline indicates SpeI site)(SEQ ID NO: 31)

| MK3-2 | ATGGAT<u>ACTA GT</u>GGTGCAGC ATCAGCCC |

EXAMPLE 5
(Preparation of mouse antibody variable region plasmid library)

Spleen of BALB/c mouse, female, was dissected and hemolysis was made by adding 5 ml of hemolytic buffer ($NH_4$ Cl 8.29 g/l, $KHCO_3$ 1.0 g/l, EDTA 3.67 g/l, pH 7.4), washed twice with 10 ml of PBS(−) to prepare lymphocytes. The mRNA was extracted from the lymphocytes and cDNA was synthesized to prepare a template for PCR. Extraction of mRNA was performed in use of mRNA purification kit (Pharmacia Inc.) and synthesis of cDNA was made in use of cDNA synthesis kit (Boehringer Mannheim A.G.). PCR was perfomed in use of the primers shown in Tables 1 and 2 to prepare H-chain and κ chain variable region fragments in each subgroup. In mouse, κ chain is a major of L-chain, consequently only κ chain was prepared as a L-chain. Since a complementary sequence from 3' terminus of $J_H$ gene to 5' terminus of $C\gamma_1$ in mouse was used as a forward primer, preparation of H-chain was limited in a variable region of IgG1 subclass antibody. In each of H-chain abed κ chain, each subgroup was mixed in equivalent to use in the forthcoming operation. XhoI site and SpeI site were introduced in the reverse primer and the forward primer, respectively, in the κ chain variable region. A PCR product of the κ chain variable region was inserted into pSEL in these restriction enzyme sites to prepare mouse κ chain variable region library (MVKL). Similarly, the H-chain variable region fragment was inserted into MVKL at BamHI site in the reverse primer and ApaI site in the forward primer to prepare mouse antibody variable region library (MVL).

EXAMPLE 6
(A trial experiment for concentrating antibody variable region fragment with specific antigen binding-activity)

M21 mouse anti-rat IgG2b antibody (IgG1κ) was used as a model antibody. A trace amount of pSELM21 prepared in Example 4 was mixed to MVL prepared in Example 5 and the mixture was introduced into COS7 cells by electroporation. The possibilities on selective concentration of the COS7 cells per se which expressed M21 chimera antibody from COS7 cells expressing various antibodies were examined. COS7 cells transformed with the plasmid were stained by biotin-labelled GK1.5 (rat IgG2b) and PE-labelled streptoavidin and sorting out the cells in use of EPICS Elite. Positive cells were sorted from approximately $6.4 \times 10^6$ cells. Plasmid DNA was recovered from the separated COS7 cells by Hirt method and introduced into E. coli DH5. Competent High E. coli DHS (TOYOBO) was used in the transformation according to the attached protocol. Appeared colonies were transferred to nylon membrane (Hybond-N, Amersham Inc.), and subjected to colony hybridization in use of M21 H-chain variable region nucleotide sequence specific oligo-nucleotide probe (M21H2: 5'-GTAGGAGAGGCTTATTACTA-3') (SEQ ID NO: 32) and κ chain variable region nucleotide sequence specific oligonucleotide probe (M21K2: 5'-AAGTATGCATCCAACCTAGA-3') (SEQ ID NO: 33) to count a ratio of pSELM21. Colony hybridization was performed in use of the probes with labelled digoxigenin (DIG oligo-nucleotide 3' endolabelling kit was used. Boehringer Mannheim A.G.: Cat. No. 1362372). Detection of probe was performed in use of DIG Luminescent Detection kit for nucleic acid detection (Boehringer Mannheim Cat. No. 1363514). The operation was followed according to the protocol. Double positive colonies in these two probes were determined to be the transformant containing pSELM21. Rate of concentration was calculated by a change in the ratio of pSELM21 transformant in the total transformants in pre-and post-sorting. In hybridization, double positive colonies in the frequency of 2/2107 could be concentrated to 54-fold in that of 10/195. (Table 3)

TABLE 3

| Sorting | Total No. of colony | No. of double positive colonies | Concentration rate |
|---|---|---|---|
| before | 2107 | 2 | |
| after | 195 | 10 | 54 |

EXAMPLE 7
(Preparation of human antibody variable region plasmid library)

Hepatitis B vaccine (Bimmugen)(Chemotherapy and Serotherapy Laboratories Inc.) was administered in a volunteer with positive anti-HBs antibody and peripheral blood 150 ml was collected after 6 days. After lymphocyte fraction was prepared by conventional method using Ficoll, mRNA was extracted and cDNA was synthesized to prepare template for PCR. Lymphocytes preparation using Ficoll is described in the reference (New Biochemistry Experiments Series 12: Molecular Immunology, Chapter 1, Isolation of lymphocytes, by K. Nishikawa). Extraction of mRNA was performed in use of mRNA purification kit (Pharmacia Inc.) and synthesis of cDNA was made in use of cDNA synthesis kit (Pharmacia Inc.). Since, in the present experiment, gene source was selected from the subject with high anti-HBs antibody titer, and anti HBs antibody would sufficiently be contained in a library containing merely κ chain in L-chain, only κ chain was selected in L-chain in the present library. PCR was performed in use of specific primer for each subgroup in Tables 4 and 5. Conditions on PCR for H-chain variable region nucleotide sequence: at 94° C. for 1 min.→at 69° C. for 1 min.→at 72° C. for 1 min., in 30 cycles, $Mg^{2+}$ conc. 0.5 mM. Referring to number of germ line $V_H$ gene contained in each subgroup, the amplified products by PCR from each subgroup of H-chain variable region nucleotide sequence were mixed together at the ratio of I:II:III:=2:3:4. In κ chain variable region nucleotide sequence, PCR products of each subgroup were mixed together at a ratio of I:IIA:IIB:III:IV=15:8:2:5:1.

XhoI site and SpeI site were introduced in the reverse primer and the forward primer for amplifying κ chain variable region nucleotide sequence, respectively. Then PCR product of κ chain variable region was digested by these restriction enzymes and ligated into pSE digested by the same enzyme. Ligated product was recovered from ethanol precipitation and was introduced into E. coli DH5 by electroporation. Electroporation was conducted by E. coli Pulser, Bio-Rad Inc. according to the attached protocol. Transformed E. coli was spread on a LB plate containing ampicillin and cultured for overnight. The colonies (approximately $7 \times 10^4$ cells) were recovered and cultured in terrific broth for overnight. Plasmid DNA was extracted and purified to prepare human Vκ gene library (pSEhVKmix).

BamHI site and EcoRI site in the reverse primer and the forward primer for amplifying H-chain variable region nucleotide sequence, respectively, were used for insertion in pSE. Colonies, approx. $5 \times 10^5$, obtained from introduction of the ligated product into DH5 were recovered and cultured. Plasmid DNA was extracted to prepare human VH gene library (pSEhVHmix). The pSEhVKmix was digested by XhoI and SpeI to recover κ chain variable region fragment. This was ligated with pSEhVH digested by XhoI and SpeI. The ligated product was introduced into DH5, and the thus obtained approx. $5 \times 10^6$ colonies were recovered. Plasmid DNA was extracted from the cultured cells and purified to prepare human antibody variable region plasmid library (PSEhVmix).

TABLE 4

Primer for amplifying human H-chain variable region nucleotide sequence

Primer Sequence

1) Reverse primer (5' terminal primer: underline indicates BamHI site SEQ ID NOS: 34–36

```
SEH5-1  GGGGGGATCC  GCTGGTGCAG  TCCGGACCAG  AGGTG  SEQ ID NO: 34
                        T                T  GG T

SEH5-2  GGGGGGATCC  GCTACAGCAG  TCAGGCCCAG  GACTG  SEQ ID NO: 35
                      G   G        GG  TG

SEH5-3  GGGGGGATCC  GCTGGTGGAG  TCTGGAGGAG  ACGT   SEQ ID NO: 36
                        T           G      G T
```

2) Forward primer (3' terminal primer: underline indicates EcoRI site (SEQ ID NO: 37)

```
SEH3    GGGGGAATTC  ACAGTGACCA  GGGTCCCACG  CCC
                      G       G  TT G CT      G
                                    T T
```

TABLE 5

Primer for amplifying human κ chain variable region

Primer Sequence

Reverse primer (5' terminal primer: underline indicates XhoI site)(SEQ ID NOS: 38–42)

```
SEK5-1   GGGGCTCGAG  ATGACCGAGT  CTCCATCCAC  ACTG  SEQ ID NO: 38
                         G                T  TT    C

SEK5-2A  GGGGCTCGAG  ATGACCCAGA  CTCCACTCTC  CCTG  SEQ ID NO: 39
                        T  T                 T

SEK5-2B  GGGGCTCGAG  ATGACCCAGA  CTCCACTCTC  CTCA  SEQ ID NO: 40

SEK5-3   GGGGCTCGAG  ATGACGCAGT  CTCCAGCCAC  CC    SEQ ID NO: 41
```

TABLE 5-continued

Primer for amplifying human κ chain variable region

Primer Sequence

|      |          |  T        |           |  G      |      |                    |
|------|----------|-----------|-----------|---------|------|--------------------|
| SEK5-4 | GGGGCTCGAG | ATGACCCAGT | CTCCAGACTC | CCTG | SEQ ID NO: 42 |

2) Forward primer (3' terminal primer: underline indicates SpeI Site)(SEQ ID NO: 43)

| SEK3 | GGGGACTAGT | GGTGCAGCCA | CAGTACGTTT | AAT |
|------|------------|------------|------------|-----|
|      |            |            |            |  G  |

EXAMPLE 8
(Screening for human anti-HBs antibody variable region nucleotide sequence)

The fact that anti-HBs antibody variable region nucleotide sequence can be screened from pSEhVmix prepared in Example 7, has been confirmed. Antigen, yHBs antigen for research studies, was purchased from Chemotherapy and Serotherapy Institute Inc. A yHBs antigen was biotinylated in K.K. Immunology and Biology Institute and used as an antigen for screening. The pSEhVmix was introduced into COS7 cells by means of electroporation to prepare membrane-bound human antibody expressing COS7 cells library. DNA 20 μg of pSEhVmix was mixed with 4×10⁶ COS7 cells (500 μl), and pulsed twice at 3 μF, 450 V. This operation was repeated 3 times to prepare COS7 cells library. After culturing the cells in DMEM containing 10% FCS for 60 hours, COS7 cells were harvested from culture dish by adding 0.02% EDTA-PBS (−).

Biotin-labelled yHBs was diluted to 1 μg/ml with 1% BSA-PBS to use for staining of COS7 cells library. In the secondary staining PE-labelled streptoavidin (Biomeda Inc: Cat. No. P22) was used. Details of staining method were described in Example 4. Sorting of the stained COS7 cells library was performed by use of FACS Vantage attached with Macro SORT system, Becton Deckinson Inc. Sorting operation was conducted according to the attached protocol to recover PE-positive cell fraction. Plasmid DNA was recovered by Hirt method from the thus obtained PE-positive cell fraction. A half thereof was introduced into E. coli DH5 by means of electroporation. Colonies appeared on the LB plate containing 0.1% ampicillin were picked up and cultured in terrific broth for overnight, and the plasmid DNA was extracted from the culture. These concentration operations were repeated for 3 times. The plasmid DNA was introduced into E. coli DH5 by electroporation. Plasmid DNA of 38 clones in the appeared colonies was purified, and H-chain and κ chain variable region nucleotide sequence were analyzed. Sequences were analyzed in use of DNA sequencer ver. 1. 2. 0. Model 373A (Applied Biosystems Inc.) according to the attached protocol. Labelling reaction was performed with primers SEQHC (5'-CTCTTGGAGGAGGGTGCCAG-3') (SEQ ID NO:44) for H-chain and SEQLC (5'-CCAGATTTCAACTGCTCATCAGA-3') (SEQ ID NO:45) for κ chain in use of PRISM Ready Reaction DyeDeoxy Terminator Cycle Sequencing Kit (Applied Biosystems Inc.). The operation was conducted according to the attached protocol.

Figure 6:
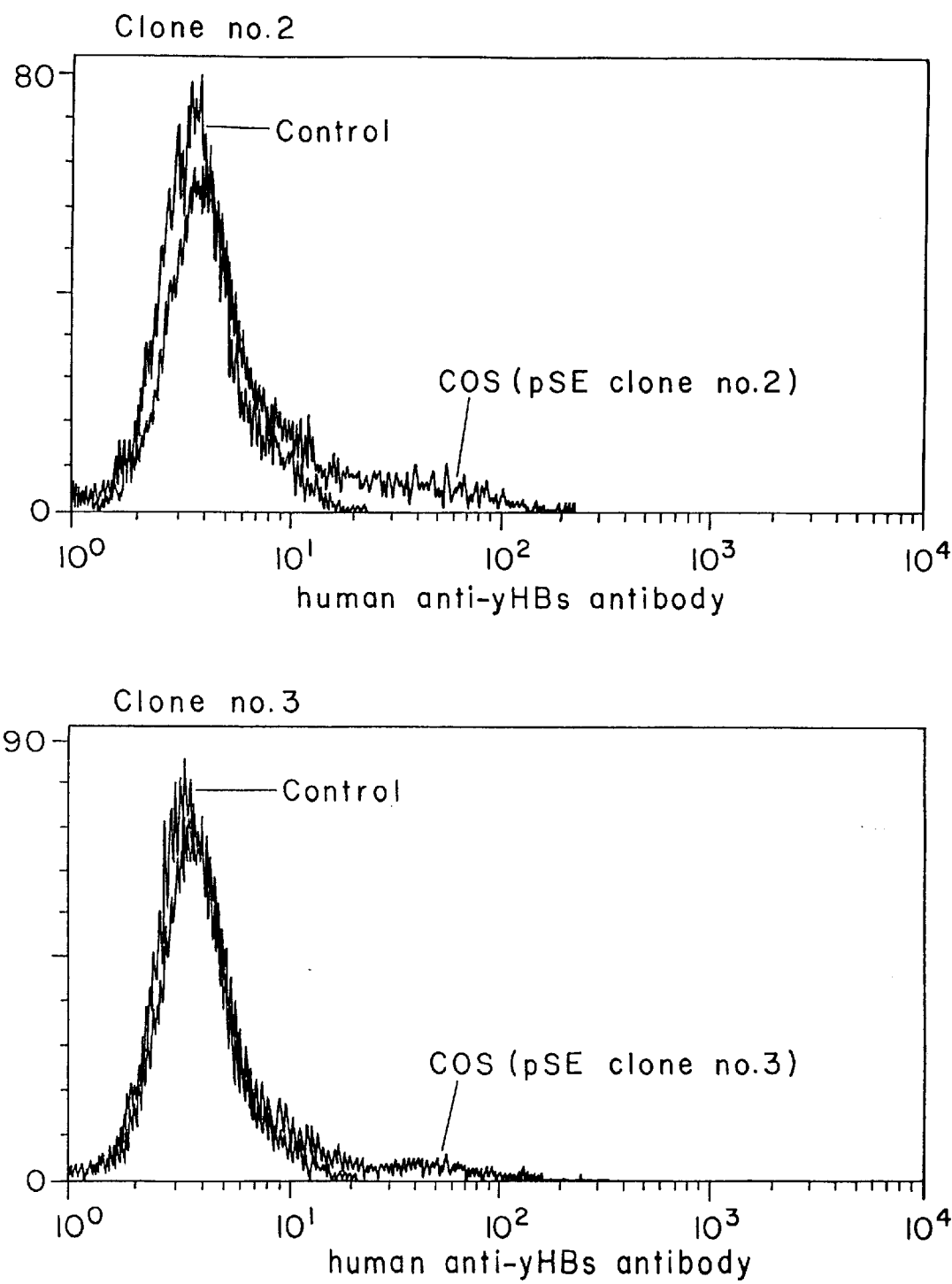
FIG. 6 shows flow cytometric analysis of binding activity for yHBs with expressed clone 2 and clone 3 in COS cells. Control: COS7 cells without transformation of the plasmid; COS (pSE clone no.2): COS cells transformed with clone 2; and COS (pSE clone no. 3): COS cells transformed with clone 3. The y-axis indicates number of cells and the x-axis indicates amount of human anti-HBs antibody expressed on COS7 cells. 12.7% of COS7 cells in which clone 2 is transformed, express human anti-yHBs antibody, and 6.6% of COS7 cells in which clone 3 is transformed, express human anti-yHBs antibody.
Figure 7:
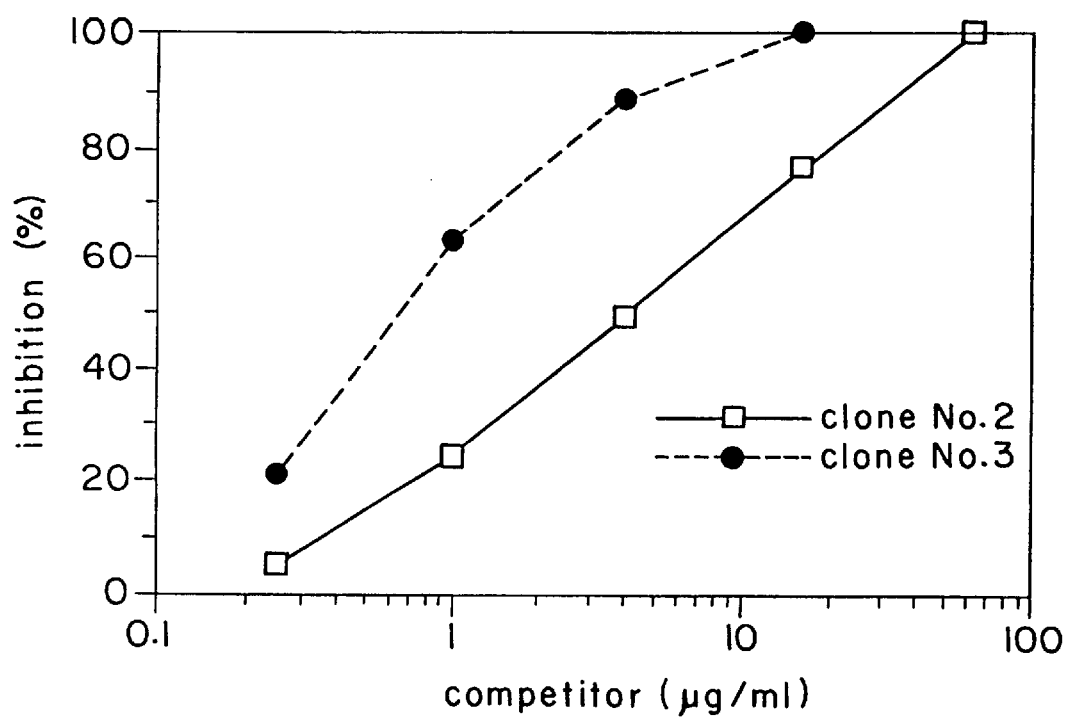
FIG. 7 shows results of competitive inhibition in use of clone 2 and clone 3.

Affinity of yHBs antigen for antibodies which were expressed on COS7 cells transformed with isolated plasmid DNA was examined. Result indicated that 29 clones in 38 clones tested bound to yHBs antigen, and the bound clones were classified in 5 indepndent clones. Result of staining of 2 clones in the 5 clones is shown in FIG. 6. Result of competitive inhibition in use of competitor yHBs without biotinylation is shown in FIG. 7. COS7 cells transformed with plasmid were reacted with various concentrations of the competitor on the ice for 30 minutes, and biotin-labelled yHBs was added at 1 μg/ml thereto, then the cells were stained conventionally. In FIG. 7, per centinhibition is shown by setting a ratio (%) of cell fraction with positive staining as 100% at the competitor concentration 0. As shown in FIG. 7, these 2 clones recognize yHBs specifically.

In the present invention, a possibility of hitherto unknown screening method for antibody variable region nucleotide sequence in use of eukaryotic cell expression system is provided. According to the present invention, variable region nucleotide sequence of antigen-specific antibody can effectively be selected with maintaining exact properties of antibody produced by animal cells. Human monoclonal antibody for any antigens can also be produced.

What is claimed is:

1. An expression vector having restriction sites to receive DNA encoding the variable regions of antibodies, said vector expressing polypeptides comprising said variable regions in the membrane-bound form on the surface of eukaryotic cells, and said vector being replicable in said cells, said vector containing at least one of the nucleotide sequences AKL and AKH:

$$5'-P_L-S_L-C_L-M_L-A_L-3' \quad (AKL)$$

$$5'-P_H-S_H-C_H-M_H-A_H-3' \quad (AKH)$$

wherein $P_L$ and $P_H$ each represent a promoter; $S_L$ and $S_H$ each represent a nucleotide sequence coding for a signal peptide; $C_L$ represents a nucleotide sequence coding for the L-chain constant region of an antibody; $C_H$ represents a nucleotide sequence coding for the H-chain constant region of an antibody or a nucleotide sequence coding for the $C_{H1}$ portion of the H-chain constant region of an antibody; $A_L$ and $A_H$ each represent a polyadenylation signal; and at least one of $M_L$ and $M_H$ represents a nucleotide sequence coding for a transmembrane domain, wherein one is $M_L$ and $M_H$ is a phosphodiester bond when the expression vector contains both AKL and AKH, and wherein AKL and AKH are free of nucleotide sequences encoding antibody variable regions and contain said restriction sites comprising sites $R1_L$, $R2_L$, $R1_H$ and $R2_H$ associated with $S_L$, $C_L$, $S_H$ and $C_H$ respectively, to facilitate insertion of nucleotide sequences coding for the L-chain and H-chain variable regions between $S_L$ and $C_L$, and $S_H$ and $C_H$, respectively.

2. The expression vector according to claim 1 wherein said cloning sites $R1_L$, $R2_L$, $R1_H$ and $R2_H$ are selected from recognition sequence of restriction enzymes MunI, AclI, BspLU11I, MluI, BssHII, NheI, XbaI, SplI, BspI407I, ClaI, XhoI, SalI and AflII.

3. The expression vector according to claim 1 wherein said transmembrane domain is the transmembrane domain of thrombomodulin.

4. The expression vector according to claim 3 wherein said expression vector contains AKL and AKH, and the cloning sites $R1_L$, $R2_L$, $R1_H$ and $R2_H$ are the recognition sequences of XhoI, SplI, ClaI and MluI, respectively, and $M_L$ is a phosphodiester bond.

5. The expression vector according to claim 3 wherein said expression vector contains AKL and AKH, and the cloning sites $R1_L$, $R2_L$, $R1_H$ and $R2_H$ are the recognition sequences of XhoI, SpeI, BamHI and EcoRI, respectively, and $M_L$ is a phosphodiester bond.

6. The expression vector according to claim 3 wherein said expression vector contains AKL and AKH, and the cloning sites $R1_L$, $R2_L$, $R1_H$ and $R2_H$ are the recognition sequences of XhoI, SpeI, BamHI and ApaI, respectively, and $M_L$ is a phosphodiester bond.

7. The expression vector according to claim 1 wherein the said vector is replicable in COS cells.

8. The expression vector of claim 1 further comprising a nucleotide sequence coding for H-chain variable region of antibodies or a nucleotide sequence coding for L-chain variable region of antibodies inserted into the cloning sites of said vector.

9. A group of eukaryotic cells expressing polypeptides containing the H-chain and L-chain variable regions of antibodies in the membrane-bound form on the surface of the cells transfected with the vector of claim 8.

10. A method for selecting nucleotide sequences coding for antibody variable regions binding to a specific antigen from the nucleotide sequences coding for a large number of antibody variable regions, comprising:

contacting the cells of claim 9 with an antigen, isolating the cells bound to said antigen from the remaining cells, and recovering the expression vector from the isolated cells to obtain nucleotide sequences coding for antibody variable regions bound to the said antigen.

11. The method according to claim 10 comprising immobilizing the antigen on a solid surface.

12. The method according to claim 10 comprising labelling the antigen with fluorescent substance, biotin or magnetic beads.

13. A plasmid vector pSEL (FERM BP-4896).

14. A plasmid vector pSE (FERM BP-4894).

15. A plasmid vector pSE2 (FERM BP-4895).

16. The method according to claim 10 wherein the specific antigen is hepatitis B antigen.

17. A kit for screening nucleotide sequences coding for variable regions of the antigen-specific antibody comprising the expression vector of claim 1, host cells and auxiliary components.

* * * * *

SEQUENCE LISTING (1) GENERAL INFORMATION:

(iii) NUMBER OF SEQUENCES: 45

(2) INFORMATION FOR SEQ ID NO: 1:

(i) SEQUENCE CHARACTERISTICS:
      (A) LENGTH: 16 base pairs
      (B) TYPE: nucleic acid
      (C) STRANDEDNESS: single (D) TOPOLOGY: linear (ii) MOLECULE TYPE: cDNA (xi) SEQUENCE DESCRIPTION: SEQ ID NO: 1:

GTCCCAGGAT CCCCGG                                                          16

(2) INFORMATION FOR SEQ ID NO: 2:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

CCGATGGGCC CTTGGTGGAG GCTGAATTCA CGGTGACCGT GGTCC                          45

(2) INFORMATION FOR SEQ ID NO: 3:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

TTTTAAGCTT GAACATGAAA CACCTGTGGT T                                         31

(2) INFORMATION FOR SEQ ID NO: 4:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

CGATGGGCCC TTGGTGGGAG GCTGACGCGT TATAATCGAT TGGGACAGGA CCCTGACATC          60

TGGGAGCTG                                                                  69

(2) INFORMATION FOR SEQ ID NO: 5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

TCGAGAATTC GTACGGTGGC TGCACCA                                              27

(2) INFORMATION FOR SEQ ID NO: 6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

CTAGTGGTGC AGCCACCGTA CGAATTC                                    27

(2) INFORMATION FOR SEQ ID NO: 7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

GTCCCAGGAT CCGCTTCAGG AGTCAGGACC                                 30

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

GTCCCAGGAT CCGCTGAAGG AGTCAGGACC                                 30

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

GTCCCAGGAT CCGCTGCAAC AATCTGGACC                                 30

(2) INFORMATION FOR SEQ ID NO: 10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

GTCCCAGGAT CCACTGCAGC AGCCTGGGGC                                 30

(2) INFORMATION FOR SEQ ID NO: 11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

GTCCCAGGAT CCGCTGGTGG AATCTGGAGG                        30

(2) INFORMATION FOR SEQ ID NO: 12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

GTCCCAGGAT CCGCTTCTCG AGTCTGGAGG                        30

(2) INFORMATION FOR SEQ ID NO: 13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

GTCCCAGGAT CCGCTTGAGG AGTCTGGAGG                        30

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

GTCCCAGGAT CCGCTGGTGG AGTCTGGGGG                        30

(2) INFORMATION FOR SEQ ID NO: 15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

GTCCCAGGAT CCGCTCGTGG AGTCTGGGGG                        30

(2) INFORMATION FOR SEQ ID NO: 16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

GTCCCAGGAT CCGTTGGTAC AGTCTGGACC                        30

(2) INFORMATION FOR SEQ ID NO: 17:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 17:

ACAGATGGGC CCGTCGTTTT GGCTGAGGAG A                            31

(2) INFORMATION FOR SEQ ID NO: 18:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

ACAGATGGGC CCGTCGTTTT GGCTGCAGAG A                            31

(2) INFORMATION FOR SEQ ID NO: 19:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

TGTGCCCTCG AGATGACACA GTCTCCATCC T                            31

(2) INFORMATION FOR SEQ ID NO: 20:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

TGTGCCCTCG AGATGACCCA AACTCCACTC TC                           32

(2) INFORMATION FOR SEQ ID NO: 21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

TGTGCCCTCG AGATGACGCA GGCTGCATTC T                            31

(2) INFORMATION FOR SEQ ID NO: 22:

(i) SEQUENCE CHARACTERISTICS:
        (A) LENGTH: 32 base pairs
        (B) TYPE: nucleic acid (C) STRANDEDNESS: single
                (D) TOPOLOGY: linear (ii) MOLECULE TYPE: cDNA (xi) SEQUENCE DESCRIPTION: SEQ ID NO: 22:

TGTGCCCTCG AGATAACCCA GGATGAACTC TC                                32

(2) INFORMATION FOR SEQ ID NO: 23:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO: 23:

TGTGCCCTCG AGCTGACCCA ATCTCCAGCT                                   30

(2) INFORMATION FOR SEQ ID NO: 24:

(i) SEQUENCE CHARACTERISTICS:
                (A) LENGTH: 29 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO: 24:

TGTGCCCTCG AGCTCACCCA GTCTCCAGC                                    29

(2) INFORMATION FOR SEQ ID NO: 25:

(i) SEQUENCE CHARACTERISTICS:
                (A) LENGTH: 32 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO: 25:

TGTGCCCTCG AGATGACACA GACTACATCC TC                                32

(2) INFORMATION FOR SEQ ID NO: 26:

(i) SEQUENCE CHARACTERISTICS:
                (A) LENGTH: 31 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO: 26:

TGTGCCCTCG AGATGACACA GTCTCCATCC T                                 31

(2) INFORMATION FOR SEQ ID NO: 27:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO: 27:

TGTGCCCTCG AGATGACTCA GTCTCCAGCC                                              30

(2) INFORMATION FOR SEQ ID NO: 28:

(i) SEQUENCE CHARACTERISTICS:
           (A) LENGTH: 33 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 28:

TGTGCCCTCG AGATGACCCA GTCTCCCAAA TCC                                          33

(2) INFORMATION FOR SEQ ID NO: 29:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 29:

TGTGCCCTCG AGGTGACCCA GTCTCCAGCA                                              30

(2) INFORMATION FOR SEQ ID NO: 30:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 30:

TGTGCCCTCG AGCTCACCCA GTCTCCAGC                                               29

(2) INFORMATION FOR SEQ ID NO: 31:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 31:

ATGGATACTA GTGGTGCAGC ATCAGCCC                                                28

(2) INFORMATION FOR SEQ ID NO: 32:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO: 32:

GTAGGAGAGG CTTATTACTA                                                         20

(2) INFORMATION FOR SEQ ID NO: 33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 33:

AAGTATGCAT CCAACCTAGA                                                                20

(2) INFORMATION FOR SEQ ID NO: 34:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 34:

GGGGGGATCC GCTGGTGCAG TCCGGACCAG AGGTG                                  35

(2) INFORMATION FOR SEQ ID NO: 35:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 35:

GGGGGGATCC GCTACAGCAG TCAGGCCCAG GACTG                                  35

(2) INFORMATION FOR SEQ ID NO: 36:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 36:

GGGGGGATCC GCTGGTGGAG TCTGGAGGAG ACGT                                   34

(2) INFORMATION FOR SEQ ID NO: 37:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 37:

GGGGGAATTC ACAGTGACCA GGGTCCCACG CCC                                    33

(2) INFORMATION FOR SEQ ID NO: 38:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 38:

GGGGCTCGAG ATGACCCAGT CTCCATCCAC ACTG                                    34

(2) INFORMATION FOR SEQ ID NO: 39:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 39:

GGGGCTCGAG ATGACCCAGA CTCCACTCTC CCTG                                    34

(2) INFORMATION FOR SEQ ID NO: 40:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 40:

GGGGCTCGAG ATGACCCAGA CTCCACTCTC CTCA                                    34

(2) INFORMATION FOR SEQ ID NO: 41:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 41:

GGGGCTCGAG ATGACGCAGT CTCCAGCCAC CC                                      32

(2) INFORMATION FOR SEQ ID NO: 42:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 42:

GGGGCTCGAG ATGACCCAGT CTCCAGACTC CCTG                                    34

(2) INFORMATION FOR SEQ ID NO: 43:

(i) SEQUENCE CHARACTERISTICS:
            (A) LENGTH: 33 base pairs
            (B) TYPE: nucleic acid
            (C) STRANDEDNESS: single -continued

```
        (D) TOPOLOGY: linear (ii) MOLECULE TYPE: cDNA (xi) SEQUENCE DESCRIPTION: SEQ ID NO: 43:

GGGGACTAGT GGTGCAGCCA CAGTACGTTT AAT                              33

(2) INFORMATION FOR SEQ ID NO: 44:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 44:

CTCTTGGAGG AGGGTGCCAG                                             20

(2) INFORMATION FOR SEQ ID NO: 45:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 45:

CCAGATTTCA ACTGCTCATC AGA                                         23
```